United States Patent
Ma

(10) Patent No.: US 9,717,503 B2
(45) Date of Patent: Aug. 1, 2017

(54) ELECTROLYTIC DETACHMENT FOR IMPLANT DELIVERY SYSTEMS

(71) Applicant: COVIDIEN LP, Mansfield, CA (US)

(72) Inventor: Jianlu Ma, Irvine, CA (US)

(73) Assignee: Covidien LP, Mansfield, MA (US)

( * ) Notice: Subject to any disclaimer, the term of this patent is extended or adjusted under 35 U.S.C. 154(b) by 72 days.

(21) Appl. No.: 14/708,661

(22) Filed: May 11, 2015

(65) Prior Publication Data

US 2016/0331381 A1 Nov. 17, 2016

(51) Int. Cl.
*A61B 17/12* (2006.01)
*B23K 31/02* (2006.01)
*A61B 17/00* (2006.01)
*A61B 90/00* (2016.01)

(52) U.S. Cl.
CPC .. *A61B 17/12172* (2013.01); *A61B 17/12031* (2013.01); *A61B 17/12109* (2013.01); *A61B 17/12113* (2013.01); *B23K 31/02* (2013.01); *A61B 2017/00526* (2013.01); *A61B 2017/00867* (2013.01); *A61B 2017/00929* (2013.01); *A61B 2017/12063* (2013.01); *A61B 2090/3966* (2016.02)

(58) Field of Classification Search
CPC ........ A61B 17/12172; A61B 17/12113; A61B 2017/12063; A61B 17/12168; A61B 17/1214; A61B 17/12031; B23K 31/027; B23K 31/02
USPC ....................................................... 606/200
See application file for complete search history.

(56) References Cited

U.S. PATENT DOCUMENTS

| | | | |
|---|---|---|---|
| 5,108,407 A | 4/1992 | Geremia et al. |
| 5,122,136 A | 6/1992 | Guglielmi et al. |
| 5,250,071 A | 10/1993 | Palermo |
| 5,354,295 A | 10/1994 | Guglielmi et al. |
| 5,370,653 A | 12/1994 | Cragg |
| 5,423,829 A | 6/1995 | Pham et al. |
| 5,509,411 A | 4/1996 | Littmann et al. |

(Continued)

FOREIGN PATENT DOCUMENTS

| | | |
|---|---|---|
| DE | 4445715 A1 | 6/1996 |
| DE | 10118017 | 10/2002 |

(Continued)

OTHER PUBLICATIONS

U.S. Appl. No. 14/454,930, filed Aug. 8, 2014.
(Continued)

*Primary Examiner* — Katrina Stransky
(74) *Attorney, Agent, or Firm* — Beth McMahon

(57) ABSTRACT

Detachment of an implant from a delivery assembly can be electrolytic. A distal end of a core member and a proximal end of an implant can be joined together by one or more weld joints disposed axially between the distal end and the proximal end, the one or more weld joints being further disposed at a radially outermost periphery of the distal end and a radially outermost periphery of the proximal end. Delivery of a detachable implant as described herein can include advancing, to a target location within a patient, an implant having a proximal end and being connected to a distal end of a core member by one or more weld joints, as described above, and separating the implant from the core member by corroding the one or more weld joints.

17 Claims, 8 Drawing Sheets

(56) References Cited

U.S. PATENT DOCUMENTS

| | | |
|---|---|---|
| 5,522,836 A | 6/1996 | Palermo |
| 5,540,680 A | 7/1996 | Guglielmi et al. |
| 5,624,449 A | 4/1997 | Pham et al. |
| 5,658,308 A | 8/1997 | Snyder |
| 5,690,667 A | 11/1997 | Gia |
| 5,733,329 A | 3/1998 | Wallace et al. |
| 5,743,905 A | 4/1998 | Eder et al. |
| 5,749,894 A | 5/1998 | Engelson |
| 5,766,629 A | 6/1998 | Cho et al. |
| 5,800,455 A | 9/1998 | Palermo et al. |
| 5,851,206 A | 12/1998 | Guglielmi et al. |
| 5,853,418 A | 12/1998 | Ken et al. |
| 5,855,578 A | 1/1999 | Guglielmi et al. |
| 5,891,128 A | 4/1999 | Gia et al. |
| 5,895,385 A | 4/1999 | Guglielmi et al. |
| 5,916,235 A | 6/1999 | Guglielmi |
| 5,919,187 A | 7/1999 | Guglielmi et al. |
| 5,925,037 A | 7/1999 | Guglielmi et al. |
| 5,925,059 A | 7/1999 | Palermo et al. |
| 5,928,226 A | 7/1999 | Guglielmi et al. |
| 5,935,145 A | 8/1999 | Villar et al. |
| 5,941,888 A | 8/1999 | Wallace et al. |
| 5,944,714 A | 8/1999 | Guglielmi et al. |
| 5,947,962 A | 9/1999 | Guglielmi et al. |
| 5,947,963 A | 9/1999 | Guglielmi |
| 5,964,797 A | 10/1999 | Ho |
| 5,976,126 A | 11/1999 | Guglielmi |
| 5,984,929 A | 11/1999 | Bashiri et al. |
| 6,010,498 A | 1/2000 | Guglielmi |
| 6,013,084 A | 1/2000 | Ken et al. |
| 6,059,779 A | 5/2000 | Mills |
| 6,063,070 A | 5/2000 | Eder |
| 6,063,104 A | 5/2000 | Villar et al. |
| 6,066,133 A | 5/2000 | Guglielmi et al. |
| 6,077,260 A | 6/2000 | Wheelock et al. |
| 6,083,220 A | 7/2000 | Guglielmi et al. |
| 6,123,714 A | 9/2000 | Gia et al. |
| 6,136,015 A | 10/2000 | Kurz et al. |
| 6,146,373 A | 11/2000 | Cragg et al. |
| 6,156,061 A | 12/2000 | Wallace et al. |
| 6,165,178 A | 12/2000 | Bashiri et al. |
| 6,168,592 B1 | 1/2001 | Kupiecki et al. |
| 6,168,615 B1 | 1/2001 | Ken et al. |
| 6,168,618 B1 | 1/2001 | Frantzen |
| 6,193,728 B1 | 2/2001 | Ken et al. |
| 6,238,403 B1 | 5/2001 | Greene, Jr. et al. |
| 6,241,691 B1 | 6/2001 | Ferrera et al. |
| 6,280,457 B1 | 8/2001 | Wallace et al. |
| 6,296,622 B1 | 10/2001 | Kurz et al. |
| 6,299,619 B1 | 10/2001 | Greene, Jr. et al. |
| 6,306,153 B1 | 10/2001 | Kurz et al. |
| 6,371,972 B1 | 4/2002 | Wallace et al. |
| 6,409,721 B1 | 6/2002 | Wheelock et al. |
| 6,416,373 B1 | 7/2002 | Kolb et al. |
| 6,425,893 B1 | 7/2002 | Guglielmi |
| 6,425,914 B1 | 7/2002 | Wallace et al. |
| 6,468,266 B1 | 10/2002 | Bashiri et al. |
| 6,468,301 B1 | 10/2002 | Amplatz et al. |
| 6,478,773 B1 | 11/2002 | Gandhi et al. |
| 6,485,524 B2 | 11/2002 | Strecker |
| 6,486,266 B2 | 11/2002 | Amano et al. |
| 6,511,468 B1 | 1/2003 | Cragg et al. |
| 6,533,801 B2 | 3/2003 | Wallace et al. |
| 6,558,367 B1 | 5/2003 | Cragg et al. |
| 6,589,230 B2 | 7/2003 | Gia et al. |
| 6,589,236 B2 | 7/2003 | Wheelock et al. |
| 6,602,261 B2 | 8/2003 | Greene, Jr. et al. |
| 6,620,152 B2 | 9/2003 | Guglielmi |
| 6,623,493 B2 | 9/2003 | Wallace et al. |
| 6,723,112 B2 | 4/2004 | Ho et al. |
| 6,743,251 B1 | 6/2004 | Eder |
| 6,835,185 B2 | 12/2004 | Ramzipoor et al. |
| 6,905,503 B2 | 6/2005 | Gifford, III et al. |
| 6,936,055 B1 | 8/2005 | Ken et al. |
| 6,953,473 B2 | 10/2005 | Porter |
| 6,964,657 B2 | 11/2005 | Cragg et al. |
| 6,966,892 B2 | 11/2005 | Gandhi et al. |
| 7,014,645 B2 | 3/2006 | Greene, Jr. et al. |
| 7,083,567 B2 | 8/2006 | Mawad |
| 7,128,736 B1 | 10/2006 | Abrams et al. |
| 7,166,122 B2 | 1/2007 | Aganon et al. |
| 7,169,172 B2 | 1/2007 | Levine et al. |
| 7,198,613 B2 | 4/2007 | Gandhi et al. |
| 7,238,194 B2 | 7/2007 | Monstadt et al. |
| 7,255,707 B2 | 8/2007 | Ramzipoor et al. |
| 7,300,458 B2 | 11/2007 | Henkes et al. |
| 7,323,000 B2 | 1/2008 | Monstdt et al. |
| 7,331,974 B2 | 2/2008 | Schaefer et al. |
| 7,485,122 B2 | 2/2009 | Teoh |
| 7,524,322 B2 | 4/2009 | Monstdt et al. |
| 7,608,089 B2 | 10/2009 | Wallace et al. |
| RE41,029 E | 12/2009 | Guglielmi et al. |
| 7,651,513 B2 | 1/2010 | Teoh et al. |
| 7,695,484 B2 | 4/2010 | Wallace et al. |
| 7,879,064 B2 | 2/2011 | Monstadt et al. |
| 7,896,899 B2 | 3/2011 | Patterson et al. |
| 7,938,845 B2 | 5/2011 | Aganon et al. |
| 8,002,789 B2 | 8/2011 | Ramzipoor et al. |
| RE42,756 E | 9/2011 | Guglielmi et al. |
| 8,016,869 B2 | 9/2011 | Nikolchev |
| 8,021,416 B2 | 9/2011 | Abrams |
| 8,048,104 B2 | 11/2011 | Monstadt et al. |
| RE43,311 E | 4/2012 | Wallace et al. |
| 8,157,855 B2 | 4/2012 | Eidenschink et al. |
| 8,202,292 B2 | 6/2012 | Kellett |
| 8,221,396 B2 | 7/2012 | Dehnad et al. |
| 8,221,483 B2 | 7/2012 | Ford et al. |
| 8,273,116 B2 | 9/2012 | Licata et al. |
| 8,298,256 B2 | 10/2012 | Gandhi et al. |
| 8,328,860 B2 | 12/2012 | Strauss et al. |
| 8,372,110 B2 | 2/2013 | Monstadt et al. |
| 8,398,671 B2 | 3/2013 | Chen et al. |
| 8,480,701 B2 | 7/2013 | Monstadt |
| 8,562,667 B2 | 10/2013 | Cox |
| 8,597,321 B2 | 12/2013 | Monstadt et al. |
| 8,632,584 B2 | 1/2014 | Henkes et al. |
| 8,641,746 B2 | 2/2014 | Andreas et al. |
| 8,641,777 B2 | 2/2014 | Strauss et al. |
| 8,652,163 B2 | 2/2014 | Padilla et al. |
| 8,657,870 B2 | 2/2014 | Turovskiy et al. |
| 8,715,312 B2 | 5/2014 | Burke et al. |
| 8,721,625 B2 | 5/2014 | Klint |
| 8,728,142 B2 | 5/2014 | Gandhi et al. |
| 8,777,978 B2 | 7/2014 | Strauss et al. |
| 8,777,979 B2 | 7/2014 | Shrivastava et al. |
| 8,795,320 B2 | 8/2014 | Strauss et al. |
| 8,795,321 B2 | 8/2014 | Strauss et al. |
| 8,801,747 B2 | 8/2014 | Strauss et al. |
| 8,845,676 B2 | 9/2014 | Monstadt et al. |
| 8,864,790 B2 | 10/2014 | Strauss et al. |
| 8,870,909 B2 | 10/2014 | Cox |
| 8,876,863 B2 | 11/2014 | Eskridge |
| 8,900,285 B2 | 12/2014 | Licata |
| 8,915,950 B2 | 12/2014 | Cam et al. |
| 8,926,681 B2 | 1/2015 | Levy et al. |
| 8,932,317 B2 | 1/2015 | Marks et al. |
| 8,940,011 B2 | 1/2015 | Teoh et al. |
| 8,974,509 B2 | 3/2015 | Licata |
| 8,974,513 B2 | 3/2015 | Ford et al. |
| 8,992,563 B2 | 3/2015 | Chen |
| 8,998,926 B2 | 4/2015 | Pomeranz |
| 9,039,749 B2 | 5/2015 | Shrivastava et al. |
| 9,050,095 B2 | 6/2015 | Monstadt et al. |
| 9,055,948 B2 | 6/2015 | Jaeger et al. |
| 2002/0151883 A1 | 10/2002 | Guglielmi |
| 2003/0014073 A1 | 1/2003 | Bashiri et al. |
| 2003/0040733 A1 | 2/2003 | Cragg et al. |
| 2003/0176857 A1 | 9/2003 | Lee |
| 2003/0212426 A1* | 11/2003 | Olson, Jr. ........ A61B 17/12027 606/191 |
| 2003/0225365 A1 | 12/2003 | Greff et al. |
| 2004/0002731 A1 | 1/2004 | Aganon et al. |
| 2004/0225279 A1 | 11/2004 | Raymond |
| 2004/0236344 A1 | 11/2004 | Monstadt et al. |

(56) References Cited

U.S. PATENT DOCUMENTS

| | | |
|---|---|---|
| 2005/0079196 A1 | 4/2005 | Henkes et al. |
| 2006/0036281 A1 | 2/2006 | Patterson et al. |
| 2006/0100602 A1 | 5/2006 | Klint |
| 2006/0135986 A1 | 6/2006 | Wallace et al. |
| 2006/0271097 A1 | 11/2006 | Ramzipoor et al. |
| 2007/0073334 A1 | 3/2007 | Ramzipoor |
| 2008/0045922 A1 | 2/2008 | Cragg et al. |
| 2008/0051803 A1 | 2/2008 | Monjtadt et al. |
| 2008/0103585 A1* | 5/2008 | Monstadt ......... A61B 17/12022 623/1.22 |
| 2008/0125855 A1 | 5/2008 | Henkes et al. |
| 2008/0221666 A1 | 9/2008 | Licata et al. |
| 2008/0228215 A1 | 9/2008 | Strauss et al. |
| 2008/0228216 A1 | 9/2008 | Strauss et al. |
| 2008/0319532 A1 | 12/2008 | Monstadt et al. |
| 2009/0143786 A1 | 6/2009 | Bashiri et al. |
| 2009/0227976 A1* | 9/2009 | Calabria ......... A61B 17/12022 604/500 |
| 2009/0254111 A1 | 10/2009 | Monstadt et al. |
| 2010/0023105 A1 | 1/2010 | Levy et al. |
| 2010/0030200 A1 | 2/2010 | Strauss et al. |
| 2010/0049165 A1 | 2/2010 | Sutherland et al. |
| 2010/0063572 A1 | 3/2010 | Teoh et al. |
| 2010/0076479 A1 | 3/2010 | Monstadt |
| 2010/0256666 A1 | 10/2010 | Chen et al. |
| 2010/0268204 A1 | 10/2010 | Tieu et al. |
| 2010/0331948 A1 | 12/2010 | Turovskiy et al. |
| 2011/0098814 A1 | 4/2011 | Monstadt et al. |
| 2011/0106128 A1 | 5/2011 | Chen |
| 2011/0118768 A1 | 5/2011 | Tran et al. |
| 2011/0118777 A1 | 5/2011 | Patterson et al. |
| 2011/0184453 A1 | 7/2011 | Levy et al. |
| 2012/0010648 A1 | 1/2012 | Monstadt et al. |
| 2012/0209310 A1 | 8/2012 | Chen et al. |
| 2012/0271344 A1 | 10/2012 | Ford et al. |
| 2013/0138198 A1 | 5/2013 | Aporta et al. |
| 2013/0184743 A1 | 7/2013 | Chen et al. |
| 2013/0211492 A1 | 8/2013 | Schneider et al. |
| 2014/0005651 A1 | 1/2014 | Eskridge |
| 2014/0039535 A1 | 2/2014 | Eskuri |
| 2014/0135818 A1 | 5/2014 | Gandhi et al. |
| 2014/0142608 A1 | 5/2014 | Eskridge et al. |
| 2014/0148843 A1 | 5/2014 | Strauss et al. |
| 2014/0163604 A1 | 6/2014 | Monstadt |
| 2014/0236217 A1 | 8/2014 | Gandhi et al. |
| 2014/0277092 A1 | 9/2014 | Teoh et al. |
| 2014/0277094 A1 | 9/2014 | Chen et al. |
| 2014/0288633 A1 | 9/2014 | Burke et al. |
| 2014/0371839 A1 | 12/2014 | Henkes et al. |
| 2015/0005804 A1 | 1/2015 | Franano et al. |
| 2015/0057700 A1 | 2/2015 | Chen et al. |
| 2015/0066073 A1 | 3/2015 | Ma |
| 2015/0105817 A1 | 4/2015 | Marchand et al. |
| 2015/0133990 A1 | 5/2015 | Davidson |
| 2015/0142042 A1 | 5/2015 | Cox |
| 2015/0150563 A1 | 6/2015 | Marchand et al. |
| 2015/0157331 A1 | 6/2015 | Levy et al. |
| 2015/0164665 A1 | 6/2015 | Cam et al. |
| 2015/0173771 A1 | 6/2015 | Marks et al. |

FOREIGN PATENT DOCUMENTS

| | | |
|---|---|---|
| EP | 719522 A1 | 7/1996 |
| EP | 0739606 A1 | 10/1996 |
| EP | 803230 A2 | 10/1997 |
| EP | 807410 A2 | 11/1997 |
| EP | 861634 A2 | 9/1998 |
| EP | 1005837 A2 | 6/2000 |
| EP | 1329196 A1 | 7/2003 |
| EP | 1420701 A1 | 5/2004 |
| EP | 1843710 A1 | 10/2007 |
| EP | 1884208 A1 | 2/2008 |
| EP | 1951129 A2 | 8/2008 |
| EP | 2124763 A2 | 12/2009 |
| EP | 2146651 A2 | 1/2010 |
| EP | 2227163 A1 | 9/2010 |
| EP | 2334242 A1 | 6/2011 |
| EP | 2415424 A2 | 2/2012 |
| EP | 2575697 A1 | 4/2013 |
| EP | 2668914 A1 | 12/2013 |
| EP | 2781196 A2 | 9/2014 |
| EP | 2859854 A1 | 4/2015 |
| WO | WO-91/13592 A1 | 9/1991 |
| WO | WO-95/12367 A1 | 5/1995 |
| WO | WO-99/09894 A1 | 3/1999 |
| WO | WO-01/32085 A1 | 5/2001 |
| WO | WO-2012/166804 A1 | 12/2012 |
| WO | WO-2013/119332 A2 | 8/2013 |

OTHER PUBLICATIONS

U.S. Appl. No. 14/454,880, filed Aug. 8, 2014.
U.S. Appl. No. 14/708,688, filed May 11, 2015.
European Search Report dated Oct. 5, 2016; European Application No. 16166685.4; 9 pages.

* cited by examiner

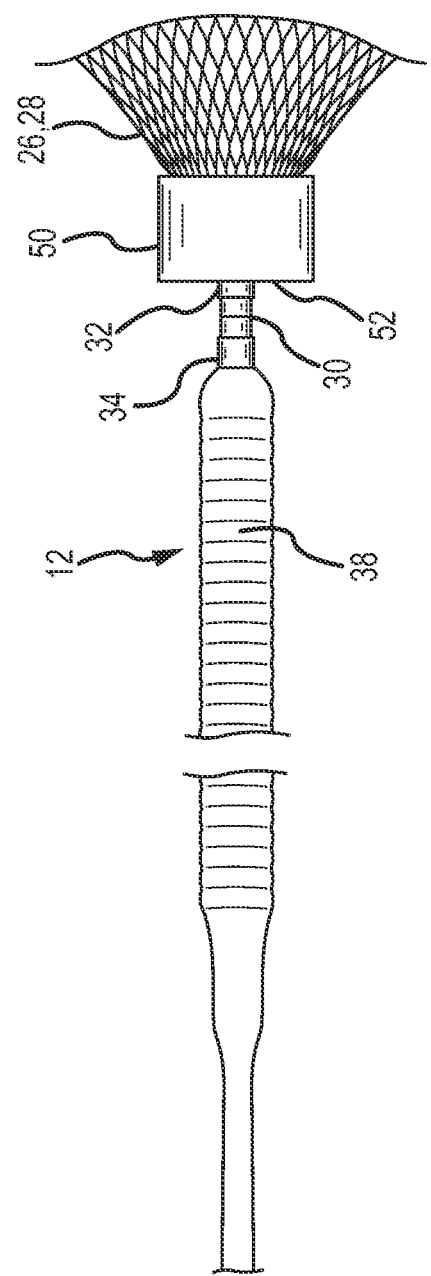

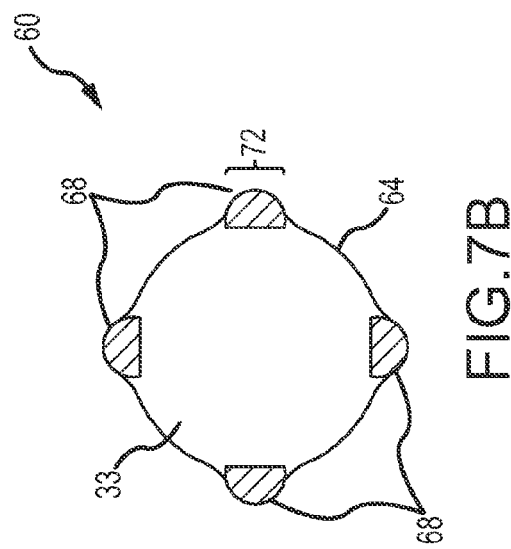
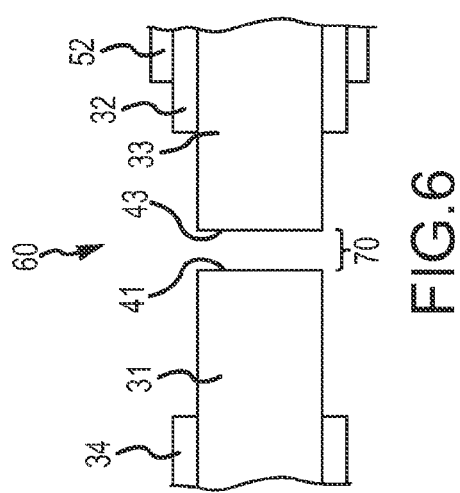
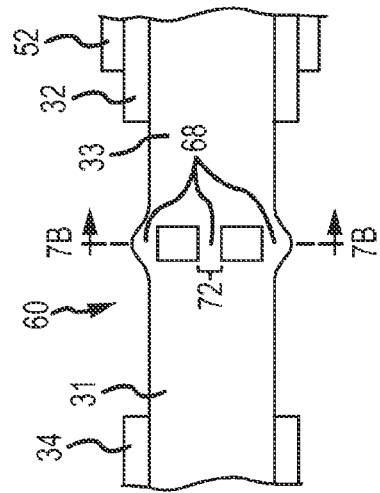

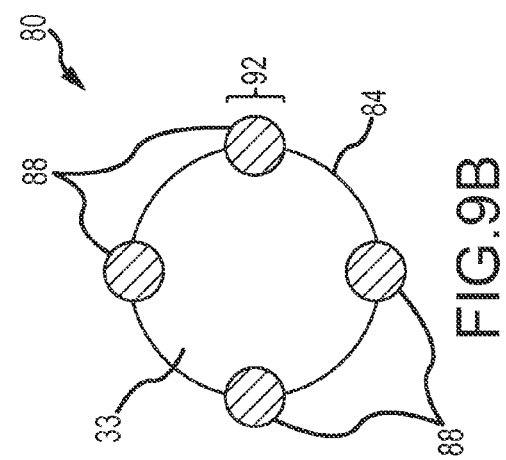
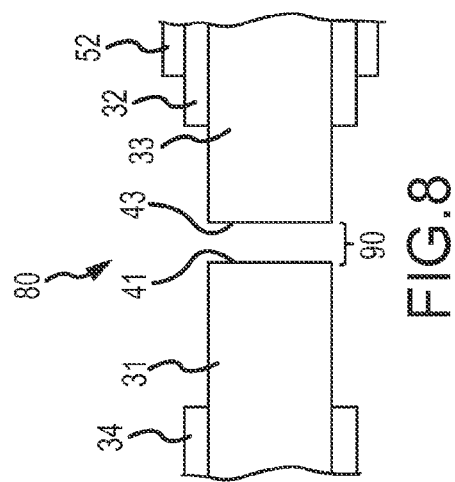
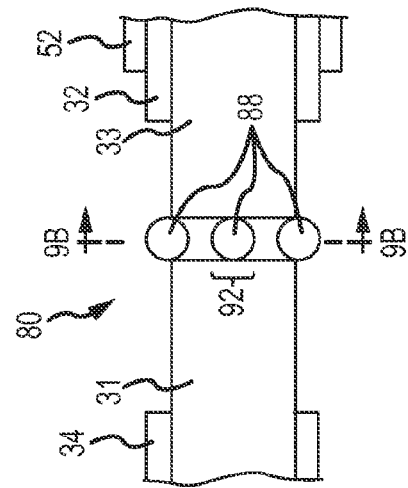

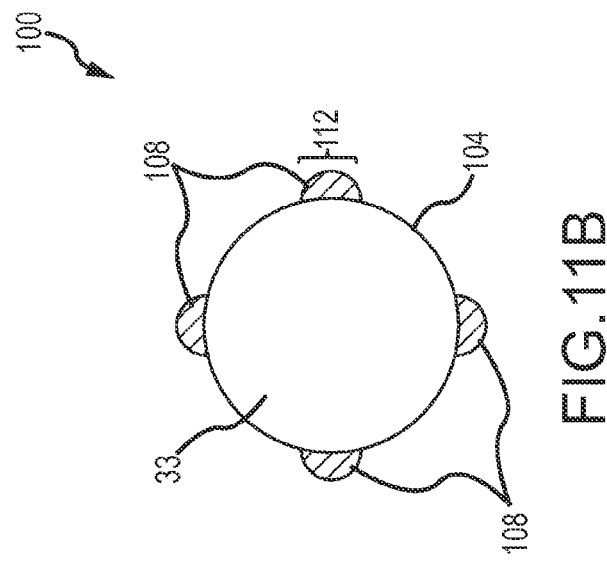
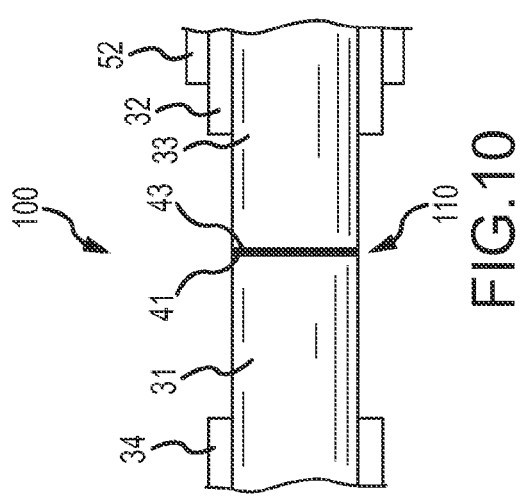
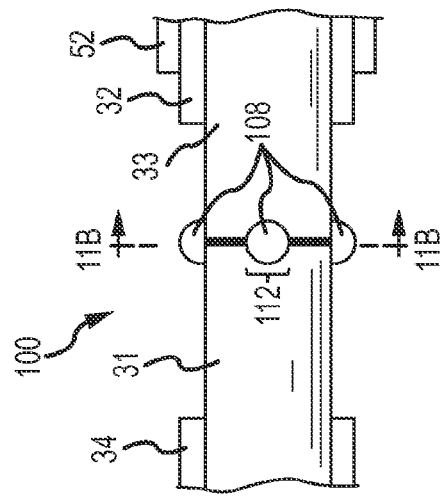

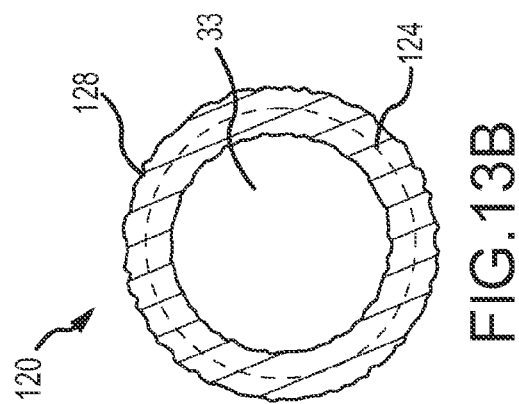
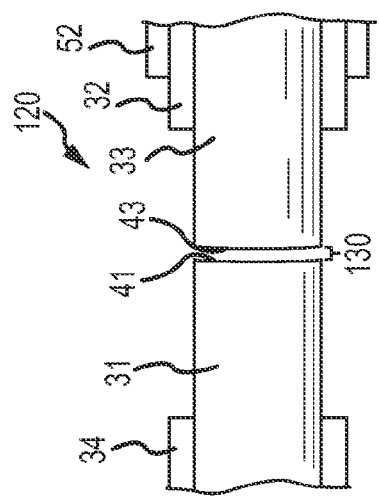
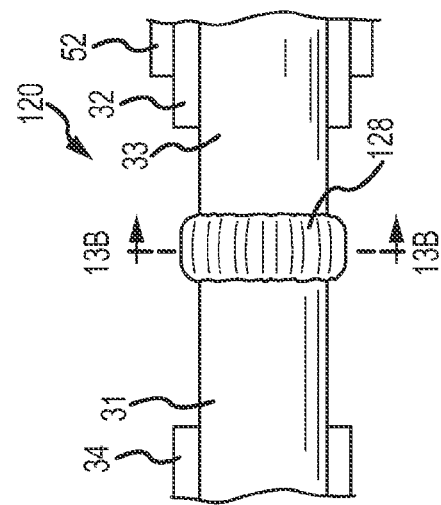

ELECTROLYTIC DETACHMENT FOR IMPLANT DELIVERY SYSTEMS

FIELD

The subject technology relates to delivery of implantable devices by a delivery system.

BACKGROUND

The use of endovascular techniques for the implantation of medical devices for the treatment and the occlusion of body cavities such as arteries, veins, fallopian tubes or vascular deformities is known in the art. For example, occlusion of vascular aneurysms can be performed using an implantable device, such as an intrasaccular implant, that is introduced with the aid of an endovascular delivery wire through a catheter. Once moved to the treatment site, the intrasaccular implant can be moved into the aneurysm cavity to occlude the aneurysm.

The severance of the implant from the delivery wire can be problematic. On the one hand, the device must be capable of forming a small profile as possible to be guided through the fine bore of the catheter to its destination, while on the other hand it must bring about a reliable severance of the implant. Absent a reliable severance of the intrasaccular implant, withdrawal of the delivery wire and catheter may cause unintended removal of the intrasaccular implant from the cavity to be occluded and thus injure and/or rupture of the wall of the cavity or vessel.

Traditional mechanical methods for the severance of implants from the insertion means are reliable. However, the necessary rigidity of the connection between the implant and the delivery means can impede the introduction of the implant. Furthermore, the low load carrying capacity of the connection due to its rigidity entails an appreciable risk of premature detachment of the insertion means from the occluding implant. Moreover, in the case of mechanical separation of the inserting wire and the implant, mechanical energy must be transmitted (e.g., by rotation of the inserting wire), which may cause the implant to be dislodged out of the correct position.

Traditional electrolytic severance of the implant involves using an electrolytically corrodible design on the end of the delivery wire at the connection between the delivery wire and the implant. Such a device can elegantly makes use of the voltage applied to the implant serving as an anode for electrothrombosis. However, the connection of the implant to the delivery wire is limited by the requirements of the electrolytically corrodible region. For example, the only materials that can be utilized are those which have a sufficiently high degree of strength to enable reliable guidance of the implant? through the delivery wire. The selection of materials for forming the point of eventual electrolytic severance is consequently extremely limited.

In the case of traditional devices for the electrolytic severance of implants, the implant and the delivery wire are not produced integrally, but instead are produced mechanically connected to each other. This design has the inherent disadvantage that the delivery wire must be tapered toward its end in an involved grinding operation in order to ensure sufficient strength in the proximal zone of the delivery wire while facilitating electrolytic, corrosive severance of the wire at the distal part of the delivery wire connected to the implant. In order to ensure sufficient strength of the connection point, the corrodible zone of the end of the delivery wire must not have a diameter below a certain minimum value since it is subjected to a high flexural load. The corrodible wire end representing the connection point between the implant and the delivery wire can be consequently extremely rigid and require a relatively long time for electrolytic corrosive severance.

SUMMARY

Electrolytic severance of an implantable medical device can involve using an electrolytically corrodible design on the end of a delivery wire at the connection between the delivery wire and the medical device.

According to some embodiments, a delivery system can comprise: a core member having a distal end; an implant, having a proximal end; and one or more weld joints disposed axially between the distal end and the proximal end, the one or more weld joints being further disposed at a radially outermost periphery of the distal end and a radially outermost periphery of the proximal end.

The one or more weld joints can be of a material more susceptible to electrolytic corrosion than each of the distal end of the core member and the proximal end of the implant. The one or more weld joints can comprise a plurality of weld joints disposed axially between the distal end and the proximal end, the plurality of weld joints being distributed about the radially outermost periphery of the distal end and the radially outermost periphery of the proximal end. The plurality of weld joints can be evenly distributed about the radially outermost periphery of the distal end and/or the radially outermost periphery of the proximal end. A radially centermost region of the distal end can be spaced apart from a radially centermost region of the proximal end by an axial gap. The distal end can connect to the proximal end only via the one or more weld joints. The one or more weld joints occupy no more than 5% of a zone (i) axially between the proximal end and the distal end and (ii) radially within the radially outermost periphery of the distal end and/or the radially outermost periphery of the proximal end. At least 95% of a zone (i) axially between the proximal end and the distal end and (ii) radially within the radially outermost periphery of the distal end and/or the radially outermost periphery of the proximal end can be a gap.

According to some embodiments, a method of delivering a detachable implant can comprise: advancing, to a target location within a patient, an implant having a proximal end and being connected to a distal end of a core member by one or more weld joints disposed axially between the distal end and the proximal end, the one or more weld joints being further disposed at a radially outermost periphery of the distal end and a radially outermost periphery of the proximal end; and separating the implant from the core member by corroding the one or more weld joints.

The separating of the implant from the core member can comprise electrolytically corroding the one or more weld joints. The separating of the implant from the core member can comprise applying an electrical current through the core member to the one or more weld joints while the one or more weld joints are in an electrolyte solution. During the separation, a radially centermost region of the distal end can be spaced apart from a radially centermost region of the proximal end by an axial gap. The advancing can comprise: advancing a distal end of a catheter, containing the implant, near the target location; and advancing the implant out of the distal end of the catheter and into the target location. The method can comprise withdrawing the core member.

According to some embodiments, a method of making a detachable implant can comprise: aligning, along a central axis, a distal end of a core member to be axially adjacent to a proximal end of an implant; and forming, at least partially from the proximal end and the distal end, one or more weld joints at a radially outermost periphery of the distal end and a radially outermost periphery of the proximal end.

The aligning can comprise maintaining an axial gap between the proximal end and the distal end. The forming can comprise applying a filler material that forms a portion of the one or more weld joints. The one or more weld joints can be at least partially of a material more susceptible to electrolytic corrosion than each of the distal end of the core member and the proximal end of the implant. The forming can comprise connecting the distal end to the proximal end only via the one or more weld joints (e.g., weld pool).

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIG. 4 shows a side view of a distal end of a delivery system, in accordance with one or more embodiments of the present disclosure.

FIG. 6 shows a side view of a detachment zone of a delivery system, in accordance with one or more embodiments of the present disclosure.

FIG. 7A shows a side view of a detachment zone of a delivery system, in accordance with one or more embodiments of the present disclosure.

FIG. 7B shows a sectional view of a detachment zone of a delivery system, in accordance with one or more embodiments of the present disclosure.

FIG. 8 shows a side view of a detachment zone of a delivery system, in accordance with one or more embodiments of the present disclosure.

FIG. 9A shows a side view of a detachment zone of a delivery system, in accordance with one or more embodiments of the present disclosure.

FIG. 9B shows a sectional view of a detachment zone of a delivery system, in accordance with one or more embodiments of the present disclosure.

FIG. 10 shows a side view of a detachment zone of a delivery system, in accordance with one or more embodiments of the present disclosure.

FIG. 11A shows a side view of a detachment zone of a delivery system, in accordance with one or more embodiments of the present disclosure.

FIG. 11B shows a sectional view of a detachment zone of a delivery system, in accordance with one or more embodiments of the present disclosure.

FIG. 12 shows a side view of a detachment zone of a delivery system, in accordance with one or more embodiments of the present disclosure.

FIG. 13A shows a side view of a detachment zone of a delivery system, in accordance with one or more embodiments of the present disclosure.

FIG. 13B shows a sectional view of a detachment zone of a delivery system, in accordance with one or more embodiments of the present disclosure.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

In accordance with some embodiments disclosed herein is the realization that detachment of an implant from a delivery assembly can be improved by enhancing features to focus the electrolytic corrosion activity. Thus, various embodiments provide for detachment zones that can facilitate electrolytic detachment of a delivery mechanism, making the detachment process faster and more reliable. For example, the total cross-sectional area of the detachment zone that must be electrolytically corroded to achieve detachment can be significantly less than a total cross-sectional area of other zones adjacent to the detachment zone, thereby decreasing the amount of time required to achieve detachment. Such improved efficiency of electrolytic detachment can be achieved while maintaining significant column strength by providing multiple points of contact between sections connected at the detachment zone. The column strength of the detachment zone facilitates a user's control and/or manipulation of the implant during use of the delivery assembly and reduces incidence of inadvertent detachment.

The implant can be implanted in body cavities or blood vessels. In addition to the implant, the delivery system can comprise a voltage source, a cathode, and a catheter. The implant can be slid in the catheter in the longitudinal direction. A delivery wire may engage the implant and be adapted to serve as an anode, such that a portion of the delivery wire is designed to be electrolytically corroded at one or more points so that while in contact with a body fluid, one or more portions of the implant may be released from the delivery wire.

Figure 1:
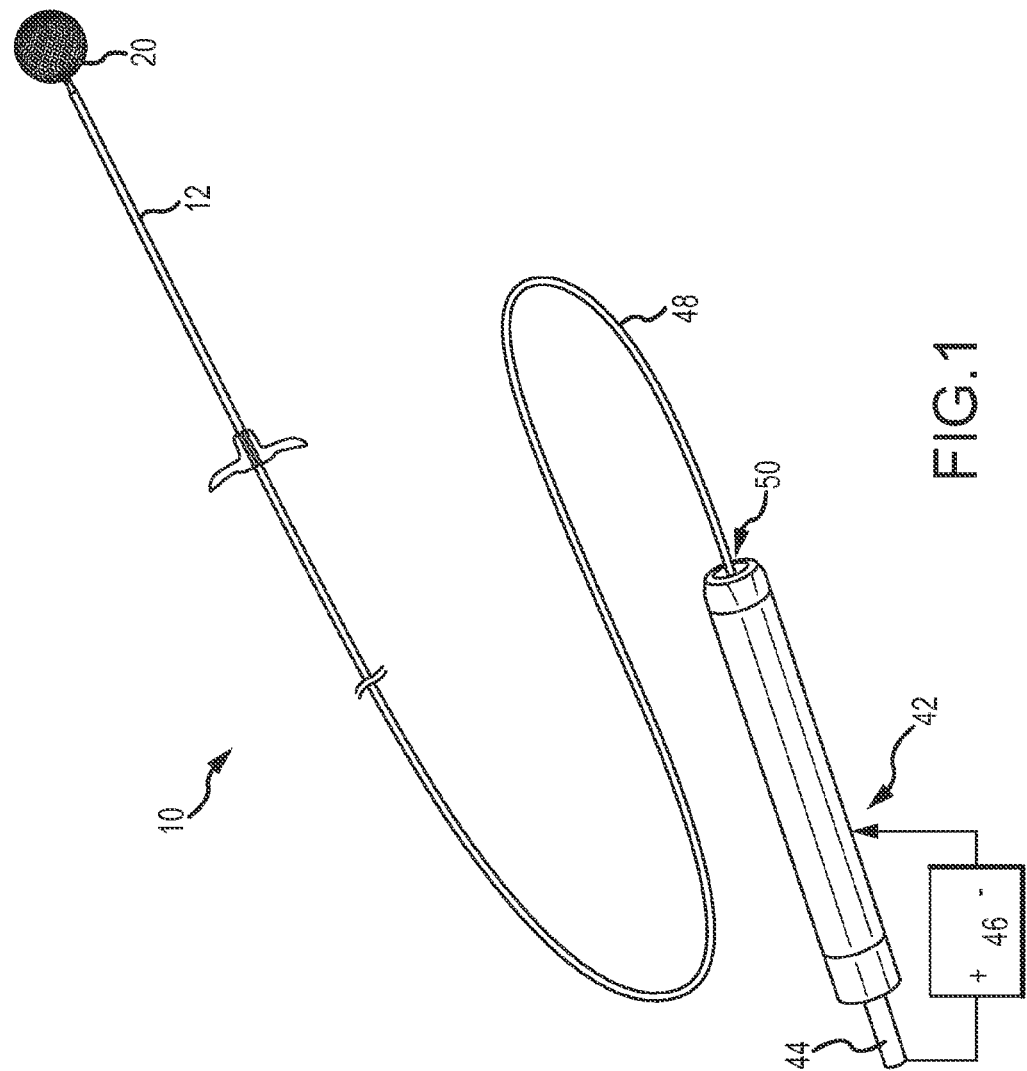
FIG. 1 shows a perspective view providing an overview of a delivery system, in accordance with one or more embodiments of the present disclosure.

According to some embodiments, FIG. 1 presents an overview of a delivery system 10 including an implant 20 and a handle 42. The handle 42 shown provides proximal access to a delivery wire 44 that engages the implant 20 at a distal end thereof. The catheter/pusher shaft 12 can include a simple extrusion (e.g., PTFE, FEP, PEEK, etc.) or can be constructed using conventional catheter construction techniques and include a liner, braid support and outer jacket (not shown). A loading sheath 48 is typically provided over the shaft of a pusher 12.

A power supply 46 may be coupled to a proximal portion of the delivery wire 44. The power supply 46 may also be coupled to a proximal portion of the handle 42 or to the patient. A current can flow from the power supply 46, to a detachment zone at or near the implant 20, and to a return path via the catheter shaft 12 (and/or another structure extending near the detachment zone. Alternatively, the current from the detachment zone may flow to the patient, and subsequently to ground or to the power supply 46. Power supply 46, for example, may be a direct current power supply, an alternating current power supply, or a power supply switchable between a direct current and an alternating current. A positive terminal of a direct current power supply, as shown in FIG. 1, may be coupled to the proximal portion of the delivery wire 44 and a negative terminal of a direct current power supply may be coupled to the proximal portion of the handle 42. Power supply 46 may provide a current through the delivery system 10 to initiate an electrolytic process during use of the assembly in a fluid medium such as a bloodstream, which may be used as an electrolyte. A power supply, such as an alternating or direct current power supply, may additionally be used to initiate an electrothrombosis process.

Figure 3:
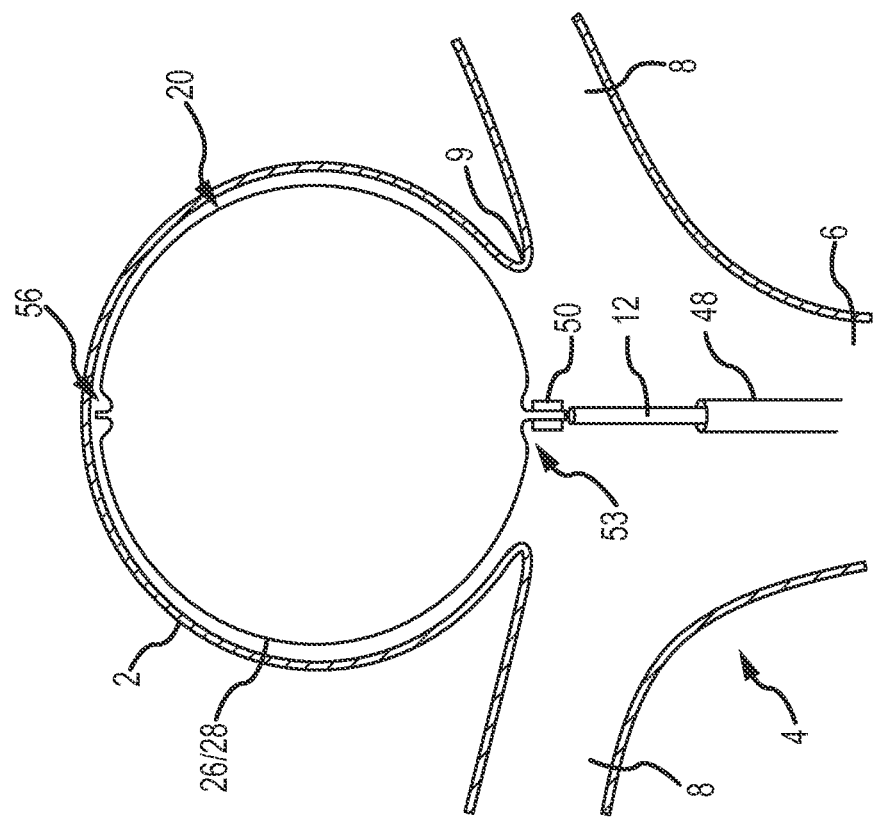
FIG. 3 shows a side-sectional view of a braid ball implant deployed within a bifurcation aneurysm, in accordance with one or more embodiments of the present disclosure.
Figure 2:
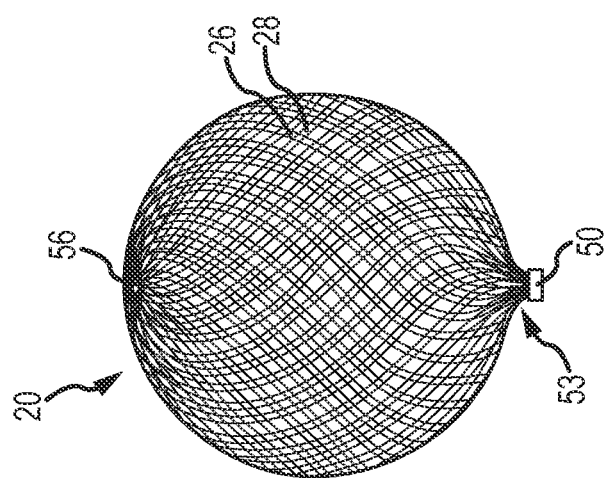
FIG. 2 shows a perspective side view of a braid ball implant, in accordance with one or more embodiments of the present disclosure.

According to some embodiments, as shown in FIGS. 2 and 3, an implant 20 delivered by the system 10 can be a braid ball implant. The braid ball implant 20 can be formed from tubular braid stock including a resilient material, such as Nitinol, that defines an open volume (generally round, spherical, ovular, heart-shaped, etc.) in an uncompressed/unconstrained state. The size of the implant can be selected to fill an aneurysm 2, so the proximal end 53 of the device helps direct blood flow along the surface of the braid from which it is constructed to the branch vessels 8. A distal end 56 of the braid ball implant 20 can be dome-shaped. The braid ball implant 20 can include a single layer or two layers 26, 28 (inner and outer layer, respectively) construction at least where impacted by flow at the neck 9 of the aneurysm 2. As shown, one or more turns of a coil (e.g., Pt wire) or a band (not shown) can provide a distal radiopaque feature to mark the location of the implant 20. Some exemplary implants that can be used in conjunction with the systems described herein are disclosed at U.S. Pub. No. 2013/0123830, published on May 16, 2013, the entirety of which is incorporated herein by reference.

According to some embodiments, the implant 20 can include a hub 50 at a proximal end 53 thereof. The hub 50 can be fixedly attached to the remainder of the implant 20. For example, the hub 50 can grasp braided filaments of the layers 26, 28 of the implant 20.

According to some embodiments, the implant 20 can be set within an aneurysm sac 2 at a vascular bifurcation 4, formed by trunk vessel 6 and efferent vessels 8. The implant 20 can be delivered by access through the trunk vessel 6 (e.g., the basilar artery), preferably through a commercially available microcatheter with a delivery system as detailed below. To deliver the implant 20, the pusher sleeve 12 is positioned such that the implant 20 can be delivered at least partially into the aneurysm sac 2. Finally, the pusher sleeve 12 is withdrawn into the delivery catheter 48.

While the implant 20 can be a braid ball implant as illustrated herein, the implant 20 can have any other form or structure, according to various embodiments. For example, the implant 20 can be a vasoocclusive coil, a cylindrical, tube-like stent, or a filter. Other types of implants and treatment devices are generally known. The subject technology can be applied to any such implant or treatment device for delivery and detachment thereof. For example, a given implant can include a hub 50 for engagement and release by a delivery system, as disclosed further herein.

Traditional electrolytic detachment members are generally a single wire with a constant diameter. These detach wires are generally as drawn and are very corrosion resistant due to the crystalline structure. Generally, when these detach wires are used they will leave behind small particulate and these particulate interfere with MRI imaging and also could lead to secondary stroke if particulate flows to distal vessel. Detachment time can be reduced by concentrating erosion to a limited area.

Figure 5:
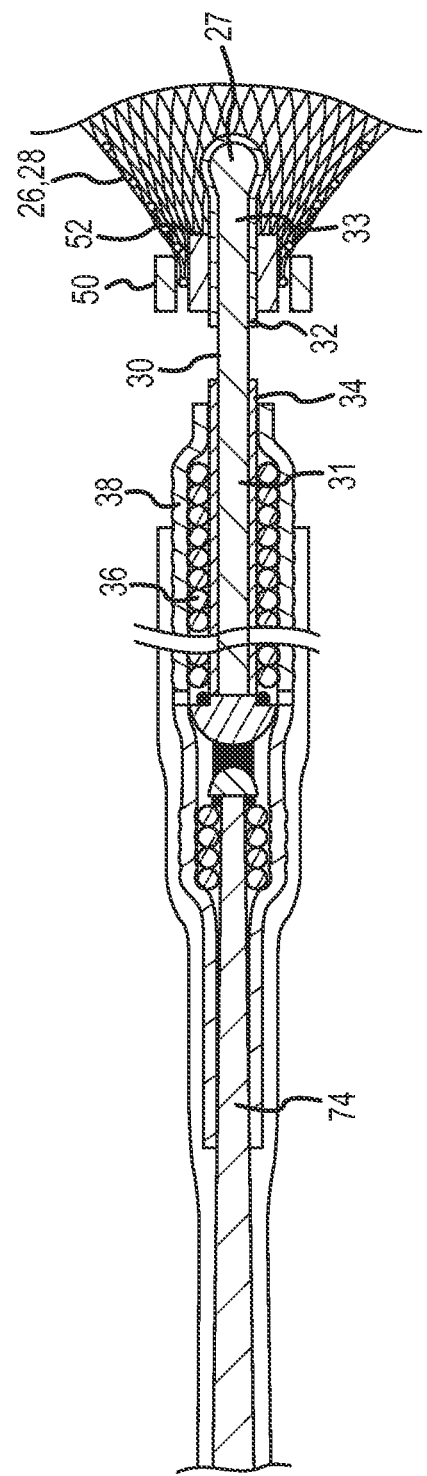
FIG. 5 shows a sectional view of a distal end of a delivery system, in accordance with one or more embodiments of the present disclosure.

According to some embodiments, as shown in FIGS. 4 and 5, a delivery system 10 includes a delivery wire 31 (e.g., core member, etc.), an implant wire 33, and a detachment zone 30 between the delivery wire 31 and the implant wire 33. The detachment zone 30 can represent the joining of a distal end 41 of the delivery wire 31 and a proximal end 43 of the implant wire 33, as best shown in FIG. 6. The types and methods of joining the delivery wire 31 and the implant wire 33 across the detachment zone 30 are discussed further herein.

According to some embodiments, portions of the delivery wire 31 can be coated with a nonconductive material. A proximal insulating layer 34 can be provided over at least a portion of an outer surface of the delivery wire 31. For example, the proximal insulating layer 34 can circumferentially surround an outer surface of the delivery wire 31. According to some embodiments, a distal insulating layer 32 can be provided over at least a portion of an outer surface of the implant wire 33. For example, the distal insulating layer 32 can circumferentially surround and contact an outer surface of the implant wire 33.

According to some embodiments, proximal and distal insulating layers 34, 32 leave exposed the detachment zone 30 between the delivery wire 31 and the implant wire 33. When in contact with a body fluid, such as blood, the fluid serves as an electrolyte allowing current to be focused on the non-coated detachment zone 30. The proximal and distal insulating layers 34, 32 prevent exposure of the delivery wire 31 and implant wire 33 to the fluid. Accordingly, electrical energy conducted along the pusher wire 74 is concentrated at the detachment zone 30, thereby reducing the time required to erode away the detachment zone 30. The proximal and distal insulating layers 34, 32 can be over-molded, co-extruded, sprayed on, or dip-coated with respect to the delivery wire 31 and/or the implant wire 33.

The proximal and distal insulating layers 34, 32 can be of an electrically nonconductive or insulative polymer, such as polyimide, polypropylene, polyolefins, combinations thereof, and the like. Laser ablation can be employed to selectively remove the coating to a controlled length minimizing the time required to erode through the component. Lengths as small as 0.0005" and as large as 0.1" or longer can be removed. According to some embodiments, lengths of detachment zone 30 can be greater than 0.005" and/or less than 0.010" to provide sufficient exposure to achieve detachment times of less than 60 seconds. Factors such as cross-sectional area, lengths, and material can be selected to regulate the detachment time to be within a desired range.

At least a portion of the delivery wire 31, the implant wire 33, and/or the detachment zone 30 can be coated with a conductive material, such as carbon, gold, platinum, tantalum, combinations thereof, and the like. One or more metallic coatings can be applied using known plating techniques.

The delivery wire 31, the implant wire 33, and/or components of the detachment zone 30, can include one or more of the following materials: ceramic materials, plastics, base metals or alloys thereof, and preferably stainless steel. Some of the most suitable material combinations for forming the electrolytically corrodible points can include one or more of the following: stainless steels, preferably of the type AISI 301, 304, 316, or subgroups thereof; Ti or TiNi alloys; Co-based alloys; noble metals; or noble metal alloys, such as Pt, Pt metals, Pt alloys, Au alloys, or Sn alloys. Further, ceramic materials and plastics employed for forming the implant can be electrically conductive.

As shown in FIG. 5, the distal insulating layer 32 electrically isolates the implant 20 from an electrical charge conducted along a length of the delivery wire 31 and the implant wire 33. A proximal end of the distal insulating layer 32 may be positioned at or proximal to the hub 50, and a distal end of the distal insulating layer 32 may be positioned at or distal to the hub 50. Likewise, a proximal end of the implant wire 33 may be positioned proximal to the hub 50, and a distal end of the implant wire 33 may be positioned within or distal to the hub 50.

According to some embodiments, as shown in FIG. 5, the delivery wire 31 can include an anchor end 27 at a terminal distal end of the delivery wire 31. The anchor end 27 can be located distal to the hub 50. For example, the anchor end 27 can be located within an interior portion of the implant 20. The anchor end 27 can have a maximum cross-sectional dimension that is greater than an inner cross-sectional dimension of an inner band 52. Accordingly, the delivery wire 31 is prevented from moving proximally entirely through the inner band 52. For example, an interface between the distal insulating layer 32 and the inner band 52 or an interface between the distal insulating layer 32 and the delivery wire 31 may allow a degree of movement of the delivery wire 31 relative to the inner band 52. To prevent the delivery wire 31 from being removed distally from within the inner band 52, the anchor end 27 can be of a size that cannot pass entirely proximally through the inner band 52.

According to some embodiments, a marker coil 36 is wound helically about an outer surface of the proximal insulating layer 34. The marker coil 36 can be of a radiopaque material, such as platinum, gold, palladium, iridium, and alloys thereof. An insulative layer 38 can be provided about an outer surface of the marker coil 36. For example, as shown in FIG. 5, the insulative layer 38 can extend over an entire length of the marker coil 36 and distally beyond the marker coil 36, such that every portion of the marker coil 36 is covered by the insulative layer 38. A distal end of the insulative layer 38 may contact and/or be adhered to the proximal insulating layer 34. The insulative layer 38 can be of an insulative biocompatible polymer material, such as polytetrafluoroethylene (PTFE). The insulative layer 38 may be shrink-wrapped over the corresponding portion of the delivery wire.

According to some embodiments, as shown in FIG. 5, a pusher wire 74 can be integrally connected to the delivery wire 31. Accordingly, an electric charge applied to the pusher wire 74 can be conducted through the pusher wire 74, the delivery wire 31, and the detachment zone 30. Furthermore, an axial force applied to the pusher wire 74 can result in an axial movement of the delivery wire 31 and the implant 20.

Referring now to FIGS. 6 and 7A-7B, with continued reference to FIGS. 1-5, illustrated are various views of an exemplary detachment zone 60, according to one or more embodiments of the subject technology. More particularly, FIG. 6 depicts a side view of the delivery wire 31 and the implant wire 33, FIG. 7A depicts a side view of the detachment zone 60 in a joined configuration, and FIG. 7B depicts a cross-sectional view of the detachment zone 60 in a joined configuration. The detachment zone 60 may be similar in some respects to the detachment zone 30 of FIGS. 4-5 and therefore may be best understood with reference thereto, where like numerals indicate like elements or components not described again in detail. Similar to the detachment zone 30 of FIGS. 4-5, for example, the detachment zone 60 may join the distal end 41 of the delivery wire 31 to the proximal end 43 of the implant wire 33.

According to some embodiments, as shown in FIG. 6, the distal end 41 of the delivery wire 31 can be brought to the proximal end 43 of the implant wire 33, to provide a gap 70 there between. The gap 70 can be any size that facilitates application of weld joints 68. For example, the gap 70 can be less than the diameter of the delivery wire 31 and/or the implant wire 33. The gap can be large enough to limit or prevent stagnation of blood between the delivery wire 31 and/or the implant wire 33. By further example, the gap 70 can be zero, where at least a portion of the delivery wire 31 contacts the implant wire 33.

According to some embodiments, as shown in FIG. 7A, one or more weld joints 68 can be formed between the distal end 41 of the delivery wire 31 and the proximal end 43 of the implant wire 33. As used herein, a weld joint refers to a structure spanning a gap to connect two structures. According to some embodiments, the weld joints 68 are formed from portions (e.g., weld pools) of the respective structures extending axially from the distal end 41 and/or another portion of the delivery wire 31 to the proximal end 43 and/or another portion of the implant wire 33.

According to some embodiments, the weld joints 68 can be formed by treating portions of the delivery wire 31 and/or the implant wire 33 to integrally combine the delivery wire 31 and/or the implant wire 33. For example, a welding device (not shown) can apply energy to the delivery wire 31 and/or the implant wire 33 at discrete locations near the gap 70 so that a portion of the delivery wire 31 contacts and coalesces with a portion of the implant wire 33. The welding device can perform its function by applying a laser beam, an electron beam, a gas flame, an electric arc, friction, and/or ultrasound. The delivery wire 31 and the implant wire 33 can coalesce at one or more weld joints 68 as portions thereof are melted, contacted, and subsequently cooled. According to some embodiments, only a portion of the delivery wire 31 is treated to coalesce with a portion of the implant wire 33. According to some embodiments, only a portion of the implant wire 33 is treated to coalesce with a portion of the delivery wire 31. According to some embodiments, both a portion of the delivery wire 31 and a portion of the implant wire 33 are treated to coalesce with each other.

According to some embodiments, as shown in FIG. 7B, some or all of the weld joints 68 are located at a radially outer periphery 64 of one or both of the delivery wire 31 and the implant wire 33. A portion of one or more weld joints 68 can extend radially outwardly from the outer periphery 64 of one or both of the delivery wire 31 and the implant wire 33. A portion of one or more weld joints 68 can extend radially inwardly from the outer periphery 64 of one or both of the delivery wire 31 and the implant wire 33.

According to some embodiments, each weld joint 68 can be circumferentially displaced from a circumferentially adjacent weld joint 68. The weld joints 68 can be distributed about a central axis with or without radial symmetry. A void or open space of the gap 70 may remain between circumferentially adjacent weld joints 68. A greater portion of the gap 70 near the outer periphery 64 may remain a void than the portion of the gap 70 that is occupied by the weld joints 68, each having a width 72.

According to some embodiments, a radially centermost region of the distal end 41 can remain spaced apart from a radially centermost region of the proximal end 43 by an axial gap. According to some embodiments, one or more weld joints 68 may also be provided at radially inward locations (not shown), such as along a central axis of the delivery wire 31 and/or the implant wire 33. FIGS. 7A-B show four weld joints 68. As will be appreciated, more or fewer than four weld joints may be provided, without departing from the scope of the disclosure. For example, the detachment zone 30 may provide 1, 2, 3, 4, 5, 6, 7, 8, 9, or more weld joints 68.

According to some embodiments, as shown in FIG. 7B, in a cross-section of the gap 70, a total area occupied by the weld joints 68 can be less than a cross-sectional area of the delivery wire 31 and/or the implant wire 33. According to some embodiments, the weld joints 68 can occupy no more than 5% of a zone (i) axially between the proximal end 43 and the distal end 41 and (ii) radially within the radially outermost periphery 64 of the distal end 41 and/or the radially outermost periphery of the proximal end 43. According to some embodiments, at least 95% of this same zone can remain a void or open space.

Referring now to FIGS. 8 and 9A-9B, with continued reference to FIGS. 1-5, illustrated are various views of an exemplary detachment zone 80, according to one or more embodiments of the subject technology. More particularly, FIG. 8 depicts a side view of the delivery wire 31 and the implant wire 33, FIG. 9A depicts a side view of the detachment zone 80 in a joined configuration, and FIG. 9B depicts a cross-sectional view of the detachment zone 80 in a joined configuration. The detachment zone 80 may be similar in some respects to the detachment zone 30 of FIGS. 4-5 and therefore may be best understood with reference thereto, where like numerals indicate like elements or components not described again in detail. Similar to the detachment zone 30 of FIGS. 4-5, for example, the detachment zone 80 may join the distal end 41 of the delivery wire 31 to the proximal end 43 of the implant wire 33.

According to some embodiments, as shown in FIGS. 6 and 8, the distal end 41 of the delivery wire 31 can be brought to the proximal end 43 of the implant wire 33, to provide a gap 90 there between. The gap 90 can be any size that facilitates application of weld joints 88. For example, the gap 90 can be less than the diameter of the delivery wire 31 and/or the implant wire 33. By further example, the gap 90 can be zero, where at least a portion of the delivery wire 31 contacts the implant wire 33.

According to some embodiments, as shown in FIG. 9A, one or more weld joints 88 can be formed between the distal end 41 of the delivery wire 31 and the proximal end 43 of the implant wire 33. According to some embodiments, the weld joints 68 are filler material, other than the material of the delivery wire 31 and the implant wire 33, that extend axially from the distal end 41 and/or another portion of the delivery wire 31 to the proximal end 43 and/or another portion of the implant wire 33.

According to some embodiments, the weld joints 88 can be formed by adding filler material between or on portions of the delivery wire 31 and portions of the implant wire 33 to bridge the gap 90. For example, a welding device (not shown) can apply energy to a filler material at the gap 90 so that the filler material contacts the delivery wire 31 and the implant wire 33 and coalesces into weld joints 88. The welding device can perform a soldering or brazing operation. By further example, the filament material can be gold, silver, or combinations thereof. For example, the filler material may have a melting point that is lower than a melting point of the delivery wire 31 and/or the implant wire 33.

According to some embodiments, as shown in FIG. 9B, some or all of the weld joints 88 are located at a radially outer periphery 84 of one or both of the delivery wire 31 and the implant wire 33. A portion of one or more weld joints 88 can extend radially outwardly from the outer periphery 84 of one or both of the delivery wire 31 and the implant wire 33. A portion of one or more weld joints 88 can extend radially inwardly from the outer periphery 84 of one or both of the delivery wire 31 and the implant wire 33.

According to some embodiments, each weld joint 88 can be circumferentially displaced from a circumferentially adjacent weld joint 88. The weld joints 88 can be distributed about a central axis with or without radial symmetry. A void or open space of the gap 90 may remain between circumferentially adjacent weld joints 68. A greater portion of the gap 90 near the outer periphery 84 may remain a void than the portion of the gap 90 that is occupied by the weld joints 68, each having a width 92.

According to some embodiments, a radially centermost region of the distal end 41 can remain spaced apart from a radially centermost region of the proximal end 43 by an axial gap. According to some embodiments, one or more weld joints 88 may also be provided at radially inward locations (not shown), such as along a central axis of the delivery wire 31 and/or the implant wire 33. FIGS. 9A-B show four weld joints 88. As will be appreciated, more or fewer than four weld joints may be provided, without departing from the scope of the disclosure. For example, the detachment zone 80 may provide 1, 2, 3, 4, 5, 6, 7, 8, 9, or more weld joints 88.

According to some embodiments, as shown in FIG. 9B, in a cross-section of the gap 90, a total area occupied by the weld joints 88 can be less than a cross-sectional area of the delivery wire 31 and/or the implant wire 33. According to some embodiments, the weld joints 88 can occupy no more than 5% of a zone (i) axially between the proximal end 43 and the distal end 41 and (ii) radially within the radially outermost periphery 84 of the distal end 41 and/or the radially outermost periphery of the proximal end 43. According to some embodiments, at least 95% of this same zone can remain a void or open space.

Referring now to FIGS. 10 and 11A-11B, with continued reference to FIGS. 1-5, illustrated are various views of an exemplary detachment zone 100, according to one or more embodiments of the subject technology. More particularly, FIG. 10 depicts a side view of the delivery wire 31 and the implant wire 33, FIG. 11A depicts a side view of the detachment zone 100 in a joined configuration, and FIG. 11B depicts a cross-sectional view of the detachment zone 100 in a joined configuration. The detachment zone 100 may be similar in some respects to the detachment zone 30 of FIGS. 4-5 and therefore may be best understood with reference thereto, where like numerals indicate like elements or components not described again in detail. Similar to the detachment zone 30 of FIGS. 4-5, for example, the detachment zone 100 may join the distal end 41 of the delivery wire 31 to the proximal end 43 of the implant wire 33.

According to some embodiments, as shown in FIG. 10, the distal end 41 of the delivery wire 31 can be brought into contact with the proximal end 43 of the implant wire 33 at a juncture 110. According to some embodiments, as shown in FIG. 11A, one or more weld joints 108 can be formed between the distal end 41 of the delivery wire 31 and the proximal end 43 of the implant wire 33. According to some embodiments, the weld joints 108 are portions (e.g., extensions or manipulated sections) of the respective structures that extend axially from the distal end 41 and/or another portion of the delivery wire 31 to the proximal end 43 and/or another portion of the implant wire 33, as described herein with respect to weld joints 68. For example, the weld joints 108 can be portions of either or both of the delivery wire 31 and the implant wire 33 that have been manipulated to extend across the juncture 110. Accordingly, the delivery wire 31 and the implant wire 33 can be connected without the addition of filler material. According to some embodiments, the weld joints 108 are filler material, other than the material of the delivery wire 31 and the implant wire 33, that extend axially from the distal end 41 and/or another portion of the delivery wire 31 to the proximal end 43 and/or another portion of the implant wire 33, as described herein with respect to weld joints 88.

According to some embodiments, as shown in FIG. 11B, some or all of the weld joints 108 are located at a radially outer periphery 104 of one or both of the delivery wire 31 and the implant wire 33. Substantially all of each weld joint 108 can extend radially outwardly from the outer periphery 104 of one or both of the delivery wire 31 and the implant wire 33. Accordingly, the weld joint 108 can be provided substantially only at an exterior surface of the outer periphery 104 of one or both of the delivery wire 31 and the implant wire 33.

According to some embodiments, each weld joint 108 can be circumferentially displaced from a circumferentially adjacent weld joint 108. The weld joints 108 can be distributed about a central axis with or without radial symmetry. FIGS. 11A-B show four weld joints 108. As will be appreciated, more or fewer than four weld joints may be provided, without departing from the scope of the disclosure. For example, the detachment zone 100 may provide 1, 2, 3, 4, 5, 6, 7, 8, 9, or more weld joints 108. According to some embodiments, as shown in FIG. 11B, at the juncture 110, a total area occupied by the weld joints 108, each having a width 112, can be less than a cross-sectional area of the delivery wire 31 and/or the implant wire 33.

Referring now to FIGS. 12 and 13A-13B, with continued reference to FIGS. 1-5, illustrated are various views of an exemplary detachment zone 120, according to one or more embodiments of the subject technology. More particularly, FIG. 12 depicts a side view of the delivery wire 31 and the implant wire 33, FIG. 13A depicts a side view of the detachment zone 120 in a joined configuration, and FIG. 7B depicts a cross-sectional view of the detachment zone 120 in a joined configuration. The detachment zone 120 may be similar in some respects to the detachment zone 30 of FIGS. 4-5 and therefore may be best understood with reference thereto, where like numerals indicate like elements or components not described again in detail. Similar to the detachment zone 30 of FIGS. 4-5, for example, the detachment zone 120 may join the distal end 41 of the delivery wire 31 to the proximal end 43 of the implant wire 33.

According to some embodiments, as shown in FIG. 12, the distal end 41 of the delivery wire 31 can be brought to the proximal end 43 of the implant wire 33, to provide a gap 130 there between. The gap 130 can be any size that facilitates application of weld joint 128. For example, the gap 130 can be less than the diameter of the delivery wire 31 and/or the implant wire 33. By further example, the gap 130 can be zero, where at least a portion of the delivery wire 31 contacts the implant wire 33.

According to some embodiments, as shown in FIG. 13A, a single, continuous, annular weld joint 128 can be formed between the distal end 41 of the delivery wire 31 and the proximal end 43 of the implant wire 33. According to some embodiments, the weld joint 128 is formed by portions of the respective structures that extend axially from the distal end 41 and/or another portion of the delivery wire 31 to the proximal end 43 and/or another portion of the implant wire 33, as described herein with respect to weld joints 68. According to some embodiments, the weld joint 128 is filler material, other than the material of the delivery wire 31 and the implant wire 33, that extend axially from the distal end 41 and/or another portion of the delivery wire 31 to the proximal end 43 and/or another portion of the implant wire 33, as described herein with respect to weld joints 88.

According to some embodiments, as shown in FIG. 13B, the weld joint 128 can extend continuously and circumferentially at or about a radially outer periphery 124 of one or both of the delivery wire 31 and the implant wire 33. A portion of the weld joint 128 can extend radially outwardly from the outer periphery 124 of one or both of the delivery wire 31 and the implant wire 33. A portion of the weld joint 128 can extend radially inwardly from the outer periphery 124 of one or both of the delivery wire 31 and the implant wire 33.

According to some embodiments, a radially centermost region of the distal end 41 can remain spaced apart from a radially centermost region of the proximal end 43 by an axial gap. According to some embodiments, as shown in FIG. 13B, in a cross-section of the gap 130, a total area occupied by the weld joint 128 can be less than a cross-sectional area of the delivery wire 31 and/or the implant wire 33.

Relative to a single monolithic wire of uniform diameter, the arrangement of weld joints 68, 88, 108, or 128 (1) decreases the amount of material that must be eroded to achieve detachment and (2) increases the exposed surface area on which erosion can occur. Furthermore, each weld joint 68, 88, 108, or 128 can be of a rigid material that maintains column strength, such that forces applied by a user to the delivery wire 31 are fully or substantially transmitted to the implant wire 33. Providing weld joints 68, 88, 108, or 128 at an outer periphery 64, 84, 104, or 124 helps resist bending at the joining of delivery wire 31 and implant wire 33.

According to some embodiments, a detachment zone 30, 60, 80, 100, or 120 can be configured such that the corrodible portion thereof defines a unique structure configured to enhance electrolytic corrosion while preserving the structural characteristics thereof. A reduction in corrosion resistance will reduce a time required to deploy an intravascular and/or intrasaccular implant, thus reducing the overall procedure time. According to some embodiments, corrosion resistance of detachment zone 30, 60, 80, 100, or 120 is decreased by exposure to laser or other energy in the formation thereof, causing the detachment zone 30, 60, 80, 100, or 120 to be structurally modified by heat. As a result, the detachment zone 30, 60, 80, 100, or 120 will have a different microstructure than the material outside of the zone (e.g., the delivery wire 31 and/or the implant wire 33). The result will decrease the time to electrolytically plate off the material, resulting in faster detachment times. Energy provided to form a detachments zone 30, 60, 80, 100, or 120 (e.g., a laser beam, an electron beam, a gas flame, an electric arc, friction, and/or ultrasound) can create surface defects for a reduction in corrosion resistance. The energy can also alter the microstructure at the detachment zone, leading to a non-uniform corrosion rate. Accordingly, the detachment zone can have a faster corrosion and detach time than that of the delivery wire 31 and/or implant wire 33.

According to some embodiments, the delivery wire 31 and/or the implant wire 33 have a microstructure with a crystallinity that is greater than a crystallinity of a microstructure of the detachment zone 30, 60, 80, 100, or 120. According to some embodiments, the detachment zone 30, 60, 80, 100, or 120 comprises a microstructure that is more amorphous than each of (i) a microstructure of the delivery wire 31 and (ii) a microstructure of the implant wire 33. According to some embodiments, a method of forming a delivery system includes providing a delivery wire 31 and an implant wire 33 and forming a detachment zone 30, 60, 80, 100, or 120 between the delivery wire 31 and the implant wire 33. In the forming thereof, the detachment zone 30, 60, 80, 100, or 120 (e.g., weld joints 68, 88, 108, or 128) achieves a microstructure that is more amorphous than each of (i) a microstructure of the delivery wire 31 and (ii) a microstructure of the implant wire 33.

According to some embodiments, weld joints 68, 88, 108, or 128 can form one or more of a variety of shapes and sizes, as shown in FIGS. 7A-7B, 9A-9B, 11A-11B, and 13A-13B. For example, the cross-sectional profile of a detachment zone 30 can define at least one concavity, valley, recess, and/or indentation formed therein. In accordance with some embodiments, the cross-sectional profile of the detachment zone can define areas of positive curvature, such as one or more peaks, protrusions, and/or convexities, with areas of negative curvature, such as one or more valleys, recesses, concavities, and/or indentations. The one or more peaks, protrusions, and/or convexities and the one or more valleys, recesses, concavities, or indentations can be formed from surface structures such as grooves, channels, pits, threads, elongate troughs, circumferential or annular grooves, slots, apertures, coils, crimped ribbon, slotted ribbon, perforated ribbon, and/or other such structures that are precisely or randomly arranged. The shape of the cross-sectional profile of the connector body can be defined by one or more linear edges, parallel linear edges, intersecting linear edges, continuous curves, and/or combinations thereof. By providing a surface structure or texture, some embodiments can thereby provide an increased surface area of the detachment zone in order to enhance the connection by weld joints 68, 88, 108, or 128, reduce the overall volume of the detachment zone, and thereby improve the rate of corrosion. Further, various embodiments can be provided that are configured to provide excellent structural characteristics in order to ensure that the detachment zone is sufficiently robust and durable. For example, in some embodiments, the component can have a component body comprising at least one structure, such as a trough, valley, recess, concavity, or indentation defining a recess surface area. In accordance with some embodiments, the component can be configured such that the valley, recess, concavity, or indentation can be used in the component without reducing structural characteristics of the component.

Further, the structure of the detachment zone can add recess surface area to the overall surface area of the detachment zone, thereby enhancing electrolytic corrosion of the detachment zone. Thus, the ratio of surface area to volume of the detachment zone can increase with an increase in overall surface area and a decrease in volume of the component. As discussed herein, the increase in the overall surface area of the detachment zone can be achieved by the incremental addition of surface area of the structure (e.g., the valley, recess, concavity, or indentation) versus the surface area of a surface without such a structure (e.g., a planar surface). The decrease in volume can be achieved by the addition of the void created by the valley, recess, concavity, or indentation.

Additionally, the detachment zone can be fabricated to provide features that will lead to an increased current density in one or more areas of the detachment zone. Such features can include, for example, ridges, edges, small radius corners, valleys, troughs, concavities, recesses, indentations, and/or other structures. In some embodiments, the presence of some of these structures on the detachment zone can reduce the local cross sectional area and/or otherwise contribute to the galvanic reaction. Features that increase current density can accelerate the galvanic reaction.

Other features and discussion of electrolytically corrodible connections is provided in other applications of the present assignee, including the discussion and disclosure of U.S. Patent Application Publication No. 2012/0010648 and U.S. Pat. Nos. 7,323,000, and 8,048,104, the entirety of each of which is incorporated herein by reference.

Electrolytically non-corrodible sections of the delivery wire can contain one or more of the following materials: noble metals or noble metal alloys, corrosion-resistant ceramic materials, corrosion-resistant plastics, and/or platinum metal alloys. The use of the above mentioned materials for the formation of electrolytically non-corrodible sections and of the electrolytically corrodible flanges ensures specific electrolytic corrosion of the flanges at the predetermined points.

In accordance with some embodiments, the electrolytically corrodible detachment zone can also be pre-corroded by etching or other methods. Thus, the structure(s) of a given cross-sectional profile can be modified to reduce the presence of corners, increase the recess depth, and/or otherwise enhance the corrosion rate. Further, various excellent structural designs can be provided to achieve desired corrosion performance through the teachings disclosed herein without pre-corrosion of the corrodible points.

Some embodiments can include a corrodible detachment zone that has a partial coating of a material to provide a greater or lesser electrochemical resistance. Thus, in embodiments that have one or more corrodible points, the electrochemical resistance of the points can be varied to achieve staged or preferential electrochemical resistance. Coatings of Zn, Sn, or alloys of such metals on fittings of stainless steel have been found to be particularly satisfactory.

Embodiments disclosed herein can be used in veterinary or human medicine and more particularly, for the endovascular treatment of intracranial aneurysms and acquired or innate arteriovenous blood vessel deformities and/or fistulas and/or for the embolization of tumors.

The apparatus and methods discussed herein are not limited to the deployment and use of an occluding device within any particular vessels, but can include any number of different types of vessels. For example, in some aspects, vessels can include arteries or veins. In some aspects, the vessels can be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some aspects, the stent delivery systems disclosed herein can be deployed within superthoracic vessels. The suprathoracic vessels can comprise at least one of intracranial vessels, cerebral arteries, and/or any branches thereof. In some aspects, the stent delivery systems disclosed herein can be deployed within intrathoracic vessels. The intrathoracic vessels can comprise the aorta or branches thereof. In some aspects, the stent delivery systems disclosed herein can be deployed within subthoracic vessels. In some aspects, the stent delivery systems disclosed herein can be deployed within lateral thoracic vessels.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A delivery system, comprising:
   a core member having a distal end;
   an implant, having a proximal end;
   an axial gap between the distal end and the proximal end;
   one or more weld joints disposed in the gap, the one or more weld joints being further disposed at a radially outermost periphery of the distal end and a radially outermost periphery of the proximal end; and
   a void in a radially centermost region of the gap.

2. The delivery system of claim 1, wherein the one or more weld joints are of a material more susceptible to electrolytic corrosion than each of the distal end of the core member and the proximal end of the implant.

3. The delivery system of claim 1, wherein the one or more weld joints comprises a plurality of weld joints disposed axially between the distal end and the proximal end, the plurality of weld joints being distributed about the radially outermost periphery of the distal end and the radially outermost periphery of the proximal end.

4. The delivery system of claim 3, wherein the plurality of weld joints are evenly distributed about the radially outermost periphery of the distal end and/or the radially outermost periphery of the proximal end.

5. The delivery system of claim 1, wherein the distal end connects to the proximal end only via the one or more weld joints.

6. The delivery system of claim 1, wherein the one or more weld joints occupy no more than 5% of a zone (i) axially between the proximal end and the distal end and (ii) radially within the radially outermost periphery of the distal end and/or the radially outermost periphery of the proximal end.

7. The delivery system of claim 1, wherein the void comprises least 95% of a zone (i) axially between the proximal end and the distal end and (ii) radially within the radially outermost periphery of the distal end and/or the radially outermost periphery of the proximal end.

8. A method of delivering a detachable implant, comprising
advancing, to a target location within a patient, an implant having a proximal end and being connected to a distal end of a core member by one or more weld joints disposed axially between the distal end and the proximal end, the one or more weld joints being further disposed at a radially outermost periphery of the distal end and a radially outermost periphery of the proximal end, the one or more weld joints defining a void between the distal end and the proximal end; and
separating the implant from the core member by corroding the one or more weld joints.

9. The method of claim 8, wherein the separating the implant from the core member comprises electrolytically corroding the one or more weld joints.

10. The method of claim 8, wherein the separating the implant from the core member comprises applying an electrical current through the core member to the one or more weld joints while the one or more weld joints are in an electrolyte solution.

11. The method of claim 8, wherein, during the separating, a radially centermost region of the distal end is spaced apart from a radially centermost region of the proximal end by an axial gap, and wherein the void is disposed in the gap.

12. The method of claim 8, wherein the advancing comprises:
advancing a distal end of a catheter, containing the implant, near the target location; and
advancing the implant out of the distal end of the catheter and into the target location.

13. The method of claim 8, further comprising withdrawing the core member.

14. A method of making a detachable implant, comprising
aligning, along a central axis, a distal end of a core member to be axially adjacent to a proximal end of an implant;
maintaining an axial gap between the proximal end and the distal end; and
forming, at least partially from the proximal end and the distal end, one or more weld joints at a radially outermost periphery of the distal end and a radially outermost periphery of the proximal end such that a void is disposed in a radially centermost region of the gap.

15. The method of claim 14, wherein the forming comprises applying a filler material that forms a portion of the one or more weld joints.

16. The method of claim 14, wherein the one or more weld joints are at least partially of a material more susceptible to electrolytic corrosion than each of the distal end of the core member and the proximal end of the implant.

17. The method of claim 14, wherein the forming comprises connecting the distal end to the proximal end only via the one or more weld joints.

* * * * *